United States Patent [19]

Larson et al.

[11] 4,269,246

[45] May 26, 1981

[54] FASTENER AND DRIVER ASSEMBLY

[75] Inventors: Eugene R. Larson; Walter Harms, both of Rockford, Ill.

[73] Assignee: Textron Inc., Providence, R.I.

[21] Appl. No.: 37,689

[22] Filed: May 10, 1979

[51] Int. Cl.³ .............................................. B25B 15/00
[52] U.S. Cl. ..................................... 81/460; 411/403
[58] Field of Search ..................................... 145/50 A

[56] References Cited

U.S. PATENT DOCUMENTS

| 2,083,092 | 6/1937 | Richer | 145/50 A |
|---|---|---|---|
| 2,182,568 | 12/1939 | Olson | 145/50 A |
| 2,366,682 | 1/1945 | West et al. | 145/50 A |
| 2,445,978 | 7/1948 | Stellin | 145/50 A |
| 2,537,029 | 1/1951 | Cambern | 145/50 A |
| 3,037,539 | 6/1962 | Johnson et al. | 145/50 A |
| 3,122,963 | 3/1964 | Borgeson | 145/50 A |
| 3,584,667 | 6/1971 | Reiland | 145/50 A |

FOREIGN PATENT DOCUMENTS 794462  5/1958  United Kingdom ................. 145/50 A Primary Examiner—Othell M. Simpson
Assistant Examiner—J. T. Zatarga

[57] ABSTRACT

There is disclosed an improved fastener and driver assembly which assures sufficient depth of engagement between the drive socket of the fastener and the working portion of the driver bit to provide efficient torque transfer from the driver to the fastener. The assembly includes a fastener having a recessed drive socket which is multi-lobular in cross-section, having an inner surface formed by alternating and smoothly joined flutes and lobes. The assembly also includes a driver for imparting rotational torque to the fastener which includes a head portion having a tip end and a center axis. The head portion of the driver is correspondingly multi-lobular in cross-section. The flutes are formed generally parallel to the center axis of the driver while the lobes of the head portion are tapered axially, converging toward the tip end of the head portion. This arrangement enables the driver head to enter the fastener socket to a predetermined depth, without binding, to thereby insure sufficient depth of engagement between the fastener lobes and the driver flutes to provide efficient torque transfer from the driver to the fastener.

4 Claims, 4 Drawing Figures

FASTENER AND DRIVER ASSEMBLY

BACKGROUND OF THE INVENTION

The present invention is directed in general to a fastener drive system, and more particularly to a new and improved fastener and driver assembly wherein the fastener includes a drive socket and the driver includes a tapered bit of novel design.

Tapered drive bits for transferring rotational torque to correspondingly structured fasteners are well known. Such arrangements find considerable application, for example, in high volume mass production assembly lines wherein a power tool having a tapered bit is used to drive fasteners into a secured position. The tapered nature of the bit enables the fastener to be engaged thereon with a slight friction fit such that the fastener will remain in mounted relation on the end of the bit until it can be engaged and driven.

Prior art drive systems i.e. socketed fastener and drive bit, or socket driven and external fasteners driving head, have taken a wide varitey of forms, two of the more common being the "hex" head and "Phillips" head types. Most systems rely upon the use of components of similar mating shape with the mating portion thereon being defined by reltively planar surfaces. While these systems have proven satisfactory for many applications, in recent years multi-lobular type drive systems have been developed, which have proved superior for use in applications involving controlled high seating torques. In this regard, the multi-lobular system, unlike many prior art designs is possessed of high efficiency in converting applied force to driving torque, and these multi-lobular systems are also effective in reducing the radial force components which tend to damage the socket element of the systems. One such multi-lobular system is illustrated in applicant's U.S. Pat. No. 3,584,667.

As a further matter, it is relatively common practice with respect to "hex" and "Phillips" type systems to employ tapered bits, in conjunction with a socket head fastener wherein the socket walls are parallel or only slightly tapered, to attain a desired degree of frictional engagement upon mounting of the fastener on the end of the bit. This feature is useful, in that the fastener will remain mounted on the bit during a moment preparatory to proper positioning of the fastener for driving. As an additional matter, use of a tapered bit serves to take up or obviate socket size variances that may be encountered. That is to say when a friction fit is obtained, the fastener is firmly engaged with the bit and will not "wobble" during driving. It has been proposed to apply this concept to multi-lobular drive systems for attainment of the same advantages. Unfortunately, however, these attempts have not proven totally successful as certain, unexpected problems have been encountered, as will be explained.

More specifically, with respect to all types of drive systems, the ability thereof to handle applied force, and convert same to driving torque is dependent upon the depth of engagement of the respective male and female components. If insufficient depth of engagement is attained between the driver bit (male component) and the fastener socket wall (female component), the material available by the socket wall to resist the force being applied by the driver bit are structurally insufficient, and the socket wall will deform under the load. The critical nature of this factor will be appreciated more fully when it is also considered that often the drive bits are formed of hardened alloy steel, while the fastener socket wall is formed of much softer varieties of steel, also a consideration is the wide variance in dimensional tolerance that is encountered between fastener and driver due to many factors, such as different manufacturers and wear of the bit and socket forming tooling in service. These tolerance variations often result in interfering engagement between the fastener and the drive occurring before the desired minimum depth of engagement is realized.

The attainment of an assured depth of engagement with multi-lobular drive systems has proven no problem where the surface portions of the mating bit and socket are disposed generally parallel to respective axis. However, where employment of a tapered, multi-lobular bit has been attempted, the results obtained have not been satisfactory, with respect to the high degree of uniform standards demanded by the fastener industry. More specifically, in inserting a tapered bit into a straight or less tapered socket, some measure of interference (i.e. friction of fit) will be attained at a certain depth of engagement. The problem is to uniformly attain this interference after the desired minimum depth of engagement is reached.

With a tapered multi-lobular drive system, the lateral or axially extending portions of the bit and socket are much increased over other designs; as for example a "hex" system. Correspondingly, any variance in dimensional tolerances which might be encountered, increases the possiblity that surface-to-surface interference or frictional engagement will occur, before the discussed depth of engagement is attained. The present invention provides a novel solution to this problem by enabling the attainment of the advantage of a tapered bit, i.e. vertical mounting of the fastener or the bit, with a greater degree of assurance of attaining the minimum depth of engagement between the driver bit and the socket.

It is therefore a general object of the present invention to provide a new and improved fastener drive system, wherein the fastener includes a drive socket, and wherein the driver, although tapered is structured for entering a fastener drive socket to a consistent and predetermined depth of engagement to assure efficient torque transfer from the driver to the fastener. The above mentioned object is achieved by providing a fastener drive system comprising, a fastener member having a drive socket, wherein said socket is multi-lobular in cross section and has an inner surface formed by alternating and smoothly joined flutes and lobes, and a driver for imparting rotational torque to the fastener and including a head portion having a tip end and a center axis. The head portion of the driver is correspondingly multi-lobular in cross-section having an outer surface formed by alternating and smoothly joined flutes and lobes for mating engagement in said fastener socket. More specifically the driver surface portions which define the base of the flutes, which it is recalled mate with the socket lobes are formed generally parallel to the center axis of the driver. On the other hand the surface portions of the bit are tapered axially, converging in a direction towards the tip end. As a result of this design the possibility of dimensional variances producing an undesired interfering engagement prior to attainment of the proper depth of engagement are substantially reduced, if not eliminated. More specifically, since the flute surface portions are substantially parallel to the bit axis attainment of premature interfering engagement along the interfaces with the socket lobe surfaces will not occur. As such the only area of possible interfering engagement is along the tapered external surface portion of the lobes. Since these lobe surface portions are external, the dimensional tolerance thereof can be controlled more readily to attain the desired mode of operation. Further, even if some dimensional variances are encountered, the likelihood of these adversely effecting the performance of the drive systems are materially reduced, since interfering engagement can occur over only a small portion of the entire surface area of the bit.

BRIEF DESCRIPTION OF THE DRAWINGS

The invention, together with the further objects and advantages thereof, may best be understood by making reference to the following description taking in conjunction with the accompanying drawings, in the several figures of which like reference numerals indicate indentical elements, and wherein.

DESCRIPTION OF A PREFERRED EMBODIMENT

Figure 1:
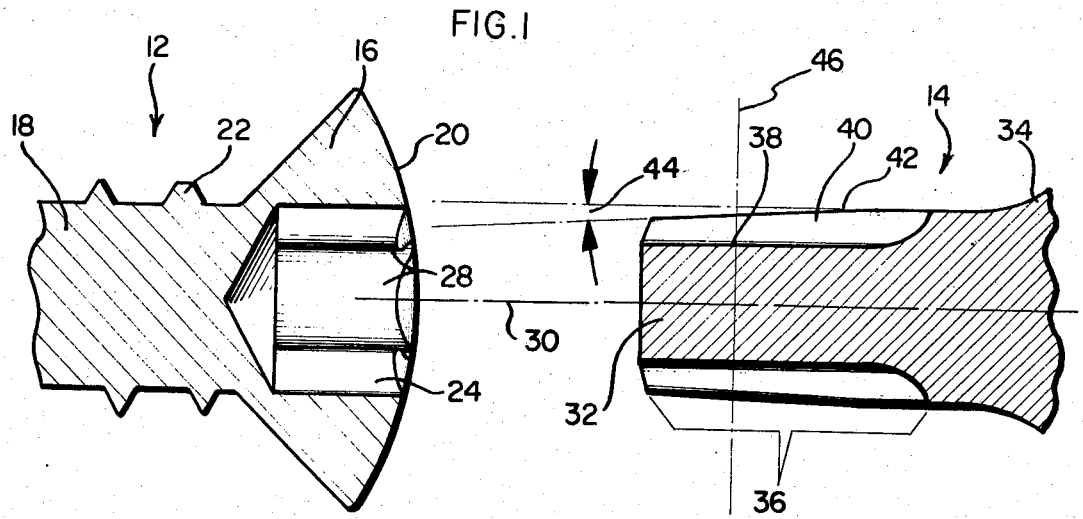
FIG. 1 is a partial cross-sectional side view illustrating a fastener and driver assembly embodying the present invention prior to the engagement of the fastener and driver.

Referring now to FIG. 1, there is shown a fastener 12 and a driver tool or bit 14 constructed in accordance with the present invention. The fastener 12 includes a head portion 16 and a shank portion 18. The head portion 16 of the illustrated embodiment is generally conical in configuration and includes a spherical end surface 20. The shank portion 18 extends from the head portion 16 and has an external thread 22 formed therein.

Figure 2:
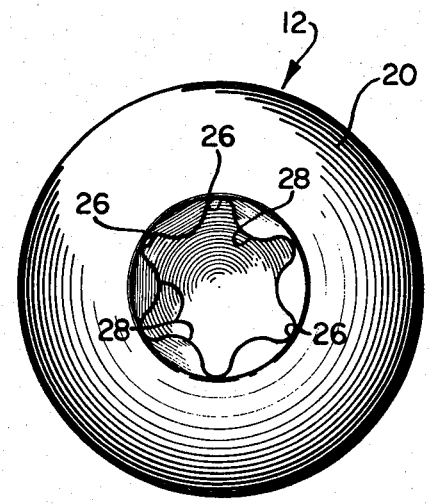
FIG. 2 is an end view of the fastener of FIG. 1 showing in greater detail the structure of the fastener drive socket.

Within the head portion 16 of the fastener 12 there is formed a drive socket 24, which as best seen in FIG. 2, is of a multi-lobular configuration. That is to say, the socket 24 has an inner surface formed by alternating and smoothly joined concaved roots or flutes 26 and convexed lobes 28. The flutes 26 and lobes 28 are defined by semi-cylindrical or substantially semi-cylindrical surfaces which extend generally parallel to the center axis 30 of the fastener 12 and driver 14. The surfaces which define the flutes 26 and lobes 28 are oppositely curved with respect to one another and alternate so as to merge smoothly with each other. Also, as will be noted from FIG. 2, the radius of curvature of the flutes 26 is less than the radius of curvature of the lobes 28.

The driver 14 includes a tip end 32 and a shank portion 34 which may be formed for engagement in the mounting jaws of a power tool or the like, or may accommodate a handle to facilitate manual operation. The portion of the driver 14 between the shank portion 34 and the tip end 32 defines a work area 36, and is that portion of the driver 14 which is utilized for engagement in the drive socket 24 of the fastener 12.

Figure 3:
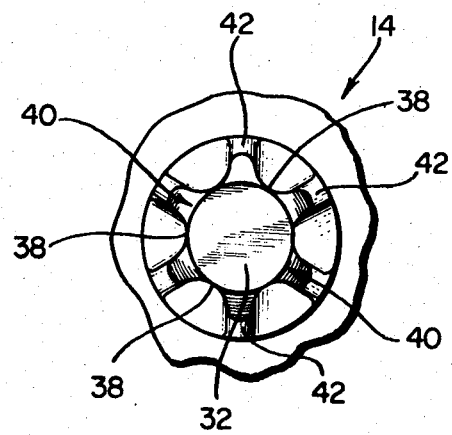
FIG. 3 is a partial end view of the driver of FIG. 1 illustrating in greater detail the structure of the driver.

As can be best seen in FIG. 3, the driver 14 is of corresponding muti-lobular configuration within the work portion 36, and includes an outer surface portion comprising first and second sets of alternating curved surfaces which merge smoothly to define a series of flutes or root portion 38 and series lobes 40. The dimension of the flutes 38 and lobes 40 of the driver 14 are substantially similar to those of the flutes 26 and lobes 28 of the fastener 12, albiet sized to permit interfilling engagement.

One of the distinguishing features of the present invention resides in the surfaces defining the driver flutes 38, as best seen in FIG. 1, are disposed generally parallel to the center axis 30 of the driver while the crest, surface portion 42 of each driver lobe 40 is tapered axially along the tip end 32, the surface converging in a direction toward said tip end. More specifically, the crest surface portion 42 of the lobes 40 are slightly tapered with respect to the center axis 30 by an angle 44 of preferably $2\frac{1}{2}°$ to $3\frac{1}{2}°$. The importance of this feature will be discussed more fully hereinafter. It should be noted further, that FIG. 1 also includes a datum line 46 which represents the location along the length of tip 32 or the datum diameter, which if received in the socket 24 will afford the minimum, desired depth of engagement.

Figure 4:
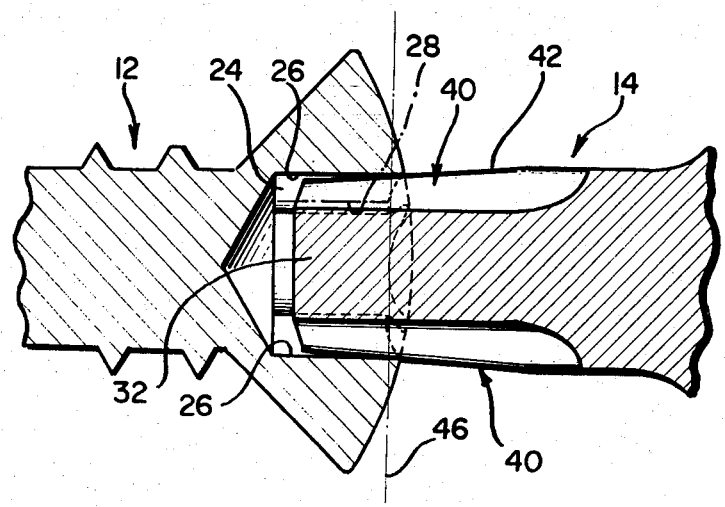
FIG. 4 is a partial cross-sectional side view of the assembly of FIG. 1 showing the fastener and driver engaged to a predetermined depth to provide efficient torque transfer from the driver to the fastener.

Referring now to FIG. 4, the driver 14 is shown engaged with the fastener 12. As can be seen, the taper of the lobes 40 permit the driver 14 to enter the fastener socket 24 until an interference or frictional fit is attained, with the datum diameter or location 46 received within the socket to assume the desired depth of engagement. Because only the lobe crest surface 42 is tapered, the dimensions of the socket 24 and the degree of taper of the lobes 40 determine the depth of engagement of the driver 14 with the fastener 12. More specifically the dimension of the driver lobes 40 adjust the tip 32 are sized to permit the tip 32 to enter the socket 24 easily. The multi-lobular tip 32 will continue to move inwardly until interferring or frictional engagement is attained along several of the lobe crest surfaces 42. This engagement is of course the engagement of the lobe crese surface 42 with an axially outer surface portion of the socket flute 26, in which the driver tip lobe 40 is engaged. Due to the fact that the socket lobes 28 (shown in dotted outline in FIG. 4) are disposed generally parallel to axis 30, i.e. non-tapered, as are the root or flute surfaces 38, no interference will result along this interface. Accordingly since the possibility of interfering engagement is limited to the crest surface portion 42, dimensional variances are less likely to prevent the driver from reaching the desired depth of engagement, as indicated by datum line 46.

As a further advantage, only one taper need be formed in producing a driver in accordance with the present invention in order to attain a consistent minimum depth of engagement. Thus, the advantages of a tapered bit are realized, with assurances that sufficient surface engagement between the drive and socket element will ensue to attain efficient torque transfer from the driver to the fastener even with fastener heads of reduced mass. As a result, stripping or reaming of the fastener drive sockets is precluded because the torque applied to the fastener drive socket by the driver will be distributed over a sufficient surface area to avoid damage to the fastener.

Although the improved fastener and driver assembly herein shown and described is structured such that the curved surfaces defined by the driver lobes are tapered axially along the work portion of the driver head towards the tip end, it of course can be appreciated that the curved surfaces defined by the driver roots or flutes could be tapered with the lobes being parallel to the driver center axis. This alternative structure would also function in accordance with the principles and features of the present invention without departing therefrom. With the driver lobes and flutes thus formed, the driver could acheive the required depth of engagement with the fastener socket, without interference, to provide efficient torque transfer from the driver to the fastener.

From the foregoing, it can be seen that the present invention provides a new and improved fastener and driver assembly. Due to the fact that only the crest lobes 42 are tapered, interference upon the insertion of the driver into the fastener drive socket is minimized to assure sufficient penetration depth of the driver for providing efficient torque transfer from the driver to the fastener. Furthermore, because only crest one surfaces 42 are tapered, forming of the driver parts to consistent manufacturing tolerances may be readily achieved to the ultimate end of providing a consistent performance of the over all drive system.

While a particular embodiment of the present invention has been shown and described, modifications may be made, and it is therefore intended to cover in the appended claims all such changes and modifications which fall within the true spirit and scope of the invention, as defined by said claims.

The invention is claimed as follows:

1. A fastener and driver combination comprising: a fastener having a recessed drive socket, said socket including a center axis and being multilobular in cross-section and having an inner surface formed by alternating and smoothly joined flutes and lobes which extend longitudinally, and essentially parallel to said socket center axis; and a driver for imparting rotational torque to said fastener and including a driving head portion having a tip end and a center axis, said driving head portion having an outer surface portion, including a plurality of axially extending flutes and lobes sized for mating engagement with the corresponding flutes and lobes of said drive socket, said driving head portion in cross-section being multi-lobular with the outer surface portion thereof comprising a first set of concaved, longitudinally extending curved surfaces and a second set of longitudinally extending convexed curved surfaces, said first and second sets of curved surfaces alternating and merging smoothly to define said plurality of axially extending flutes and lobes, with the apecies of said convexed curved surfaces defining longitudinally extending crests portions for said lobes, and the apecies of said concaved curved surfaces defining longitudinally extending trough portions for said lobes and only one of said first or second sets of curved surfaces and the crest or trough portions defined thereby being axially parallel to said center axis of said driving head portion, while the other said set of curved surfaces and the crest or trough portions defined thereby being tapered axially, such that said last mentioned tapered crest or trough portions converge in a direction toward said tip end to enable said driving head portion to enter said fastener drive socket to a predetermined depth with interferring engagement being attained only between said axially tapered crest or trough portions and the set of mating surfaces of said socket, thereby to control and insure the desired depth of engagement of said driver head portion in said drive socket while attaining a friction fit between said fastener and said driver which serves to maintain said fastener mounted on the end of said driver.

2. A fastener and driver combination as defined in claim 1 wherein the crest portions defined by said second set of generally convexed curved surfaces forming said driver lobes are tapered axially along said head toward said tip end.

3. A combination as defined in claim 2 wherein the angle of taper of said lobe crest portions of said driver head with respect to said center axis is between 2½° and 3½°.

4. A combination as defined in claim 2 wherein said fastener socket and said driver head each comprise six lobes and six flutes.

* * * * *